US006821752B2

(12) United States Patent
Sheppard

(10) Patent No.: US 6,821,752 B2
(45) Date of Patent: Nov. 23, 2004

(54) METHODS AND COMPOSITIONS FOR EXTRACTING PROTEINS FROM CELLS

(75) Inventor: Scot R. Sheppard, Clayton, NC (US)

(73) Assignee: Akzo Nobel N.V., Arnhem (NL)

( * ) Notice: Subject to any disclaimer, the term of this patent is extended or adjusted under 35 U.S.C. 154(b) by 257 days.

(21) Appl. No.: 10/052,690

(22) Filed: Jan. 18, 2002

(65) Prior Publication Data

US 2003/0003534 A1 Jan. 2, 2003

Related U.S. Application Data

(63) Continuation-in-part of application No. 09/766,043, filed on Jan. 19, 2001, now abandoned.

(51) Int. Cl.$^{7}$ .......................... C12N 21/06; C12N 1/14; C07K 14/00

(52) U.S. Cl. ................ 435/69.1; 435/255.1; 435/255.5; 435/804; 530/350; 530/412; 530/418; 530/422

(58) Field of Search ............................ 435/69.1, 255.1, 435/255.5, 804; 530/350, 412, 418, 422

(56) References Cited

U.S. PATENT DOCUMENTS 5,011,915 A * 4/1991 Yamazaki ................... 530/414
5,407,810 A * 4/1995 Builder et al. ............. 435/69.1

OTHER PUBLICATIONS

Horowitz et al., Blood, vol. 79, No. 3, pp. 826–831, 1992.*

Horowitz et al., Transfussion, vol. 25, No. 6, pp. 516–522, 1985.*

Piet et al., Transfussion, vol. 30, No. 7, pp. 591–592, 1990.*

Piet, M.P.J. et al: "The use of tri(n–butyl)phosphate detergent mixtures to inactivate hepatitis viruses and human immunodeficiency virus in plasma and plasma's subsequent fractionation" *TRANSFUSION* (1990), 30(7), 591–598.

Horowitz, B. et al: "Inactivation of viruses in labile blood derivatives" *TRANSFUSION* (1985), 25(6), 516–522.

Horowitz, Bernard et al: "Solvent/Detergent–Treated Plasma: A Virus–Inactivated Substitute for Fresh Frozen Plasma" *BLOOD* (1992), 79(3), 826–831.

Helenius, Ari et al: "Solubilization of Membranes by Detergents" *Biochimica et Biophysica Acta*, 415 (1975), 29–79, BBA 85143, The Netherlands.

* cited by examiner

*Primary Examiner*—Jon P. Weber
*Assistant Examiner*—Abdel A. Mohamed
(74) *Attorney, Agent, or Firm*—William P. Ramey, III

(57) ABSTRACT

The present invention relates to a process of releasing a protein, recombinant or otherwise, from a cell. The process of the present invention involves contacting a host cell containing a protein of interest with a solution comprising one or more detergents and one or more reducing agents. The methods of the invention are particularly suitable to large scale production of recombinant products.

17 Claims, 1 Drawing Sheet

METHODS AND COMPOSITIONS FOR EXTRACTING PROTEINS FROM CELLS

This application is a continuation-in-part of Ser. No. 09/766,043, filed Jan. 19, 2001, now abandoned.

TECHNICAL FIELD OF THE INVENTION

The present invention relates to a process of recovering intracellular proteins and other molecules from a cell.

BACKGROUND OF THE INVENTION

It is desirable to lyse cells grown as production hosts containing a protein or other molecule of interest to recover any desired intracellularly produced product. Conventional ways to kill and lyse such cells include the use of heat (U.S. Pat. No. 4,601,986 to Wegner, et al.), osmotic pressure (U.S. Pat. No. 4,299,858 to Aubert, et al), enzymes which break down the cell walls or membranes (U.S. Pat. No. 3,816,260 to Sugiyama, U.S. Pat. No. 3,890,198 to Kobayashi, et al. and U.S. Pat. No. 3,917,510 to Kitamura, et al.) and mechanical disruption of the cell wall by, for example, high pressure homogenization. The disclosures of the above patents are incorporated herein by reference.

Also, detergents have been utilized to lyse the cell wall. For example, yeast protein extraction reagent (Y-PER®), sold by Pierce Chemical Company, contains a detergent to provide a gentle means of cell lysis that is not detrimental to the protein of interest. However, Y-PER® is intended to be used as a laboratory bench reagent, not as a reagent useful for the large scale production of proteins, and is costly. For these reasons, Y-PER® has not gained acceptance as a useful reagent for the large scale production of recombinant protein from host cells.

There is a need in the art for a process that can be used to easily cause the release of proteins from host cells without harming the desired protein and with a minimum of process steps. The method of cell lysis should not directly or indirectly lead to denaturation of the desired product and the method should be consistent with subsequent processing requirements and with large scale production.

SUMMARY OF THE INVENTION

The present invention relates to a process of releasing a protein, recombinant or otherwise, from a cell. The process of the present invention involves contacting a host cell containing a protein of interest with a solution comprising one or more detergents and one or more reducing agents. The addition of one or more reducing agents facilitates the recovery of proteins in their native conformations. The methods of the invention are particularly suitable to large scale production of recombinant products. The methods of the invention comprise four basic steps: adjustment of bulk solution conditions to achieve a permissive environment, contact of cells with a reducing agent either before, during or after contact of the cells with certain charge-modified hydrocarbons, and finally clarification of the extract to produce a fraction suitable for formulation or further processing. Typically, the reducing agent and the detergent are added sequentially in any order, resulting in the concurrent exposure of the cells to the reducing agent and the detergent.

In a particular embodiment, the one or more detergents are amphipathic, charged amines or amine oxides coupled to hydrocarbon chains of varying lengths. In a preferred embodiment, the one or more detergents used are selected from the group consisting of, tributylphosphate, dimethyldecylamine, dimethyltridecylamine, dimethylundecylamine, dimethyldidecylamine, dimethytetradecylamine, dimethylhexadecylamine, dimethyldecylamineoxide, dimethylundecylamineoxide, dimethyldidecylamineoxide, dimethytetradecylamineoxide and dimethyltridecylamineoxide. Preferably, the detergent is not dimethyltridecylamine.

Detergents may be used at concentrations ranging from 0.01% up to their solubility limit. Preferably, the concentration of the detergents ranges from 0.05% to 5%, 0.1% to 2%, or is approximately 0.5% of the total solution. When added to cells suspended in buffer, the detergent is preferably at a higher concentration than the final concentration at which the cells are lysed. Preferably, the detergent is at least at a 2 fold, 5 fold, 10 fold or 100 fold higher concentration.

In a particular embodiment, the one or more reducing agents are agents are those reducing agents that reduce disulfide bonds and/or maintain sulfhydryl residues in the reduced form. Any such reducing agent or agents may be used. In a preferred embodiment, the one or more reducing agents used are selected from the group consisting of, Dithiothreitol (DTT); Dithioerythiritol (DTE); Cysteine (Cys) and Tris 2-carboxyethyphosphine (TCEP).

Reducing agents may be used at concentrations ranging from 0.1 mM to 100 mM, 1 mM to 25 mM, 2 mM to 10 mM, or about 5 mM. When added to cells suspended in buffer, the reducing agent is preferably at a higher concentration than the final concentration at which the cells are lysed. Preferably, the detergent is at least at a 2 fold, 5 fold, 10 fold or 100 fold higher concentration.

In addition to the one or more detergents and reducing agents, in a preferred embodiment, the cells are also contacted with glycerol. Preferably, the glycerol concentration is at least 0.6%, or ranges from 0.6% to 20%, 0.6% to 15%, 0.6% to 12%, 0.6% to 6%, 0.6% to 3%, or 0.6% to 1%.

The pH of the solution can range from pH 2 to pH 12. Preferably, the solution is at a pH ranging from pH 5.0 up to pH 8.0. More preferably, the pH ranges from pH 5.5 to 7.4, from pH 6 to 7.4, from pH 7.0 to 7.4, or is approximately pH 7.3.

The recovery of protein from the cells with the solution of the invention can be carried out at a temperature of from about 2° C. to about 50° C. Preferably, the temperature is from about 2° C. to about 30° C., about 2° C. to about 20° C., about 2° C. to about 10° C., about 3° C. to about 10° C., about 4° C., about 25° C., or at room temperature.

The "host cells" are cells containing a protein of interest. A "protein of interest" is any protein present in a host cell that one desires to release from the host cell and, optionally, subsequently isolate or purify. Preferably, the protein of interest is a recombinant protein. In a preferred embodiment, the protein of interest has a molecular weight of less than 100 kD. In a further preferred embodiment, the protein of interest has a molecular weight of between 5 and 75 kD, preferably about 50 kD. The host cells may be of any type, preferably mammalian, bacterial, yeast, fungal, plant, avian, or reptilian. Most preferably, the host cells are yeast cells. In a particular embodiment, the yeast cells are of the species *Pichia pastoris*.

In addition to releasing proteins from host cells, the composition of the invention may be used to release other molecules from host cells including nucleic acids, lipids, vitamins, small molecules and other cell, cytosolic, or organelle derived molecules or molecular complexes.

BRIEF DESCRIPTION OF THE DRAWINGS

The various features of the invention may be more fully understood from the following description when read together with the accompanying drawings.

—FIG. 1 shows the effect of time, temperature and reducing agent on the recovery of a protein of interest from a host cell.

DETAILED DESCRIPTION OF THE INVENTION

Figure 1:
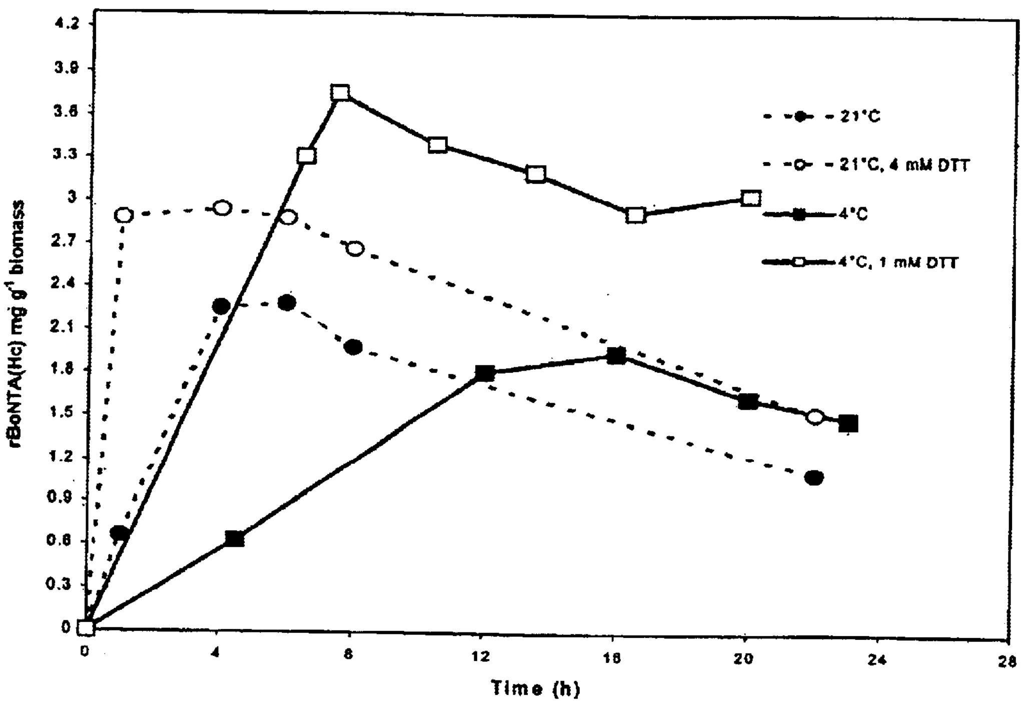
FIG. 1. Extraction of rBoNTA(Hc) with and without DTT at 4° C. and 21° C.

The present invention relates to a process of releasing a protein, recombinant or otherwise, from a cell. The methods of the invention comprise four basic steps: adjustment of bulk solution conditions to achieve a permissive environment, contact of cells with a reducing agent either before, during or after contact of the cells with certain charge-modified hydrocarbons, and finally clarification of the extract to produce a fraction suitable for formulation or further processing.

In a particular embodiment, solution conditions are adjusted by 1) sedimentation of the cellular fraction followed by re-suspension, 2) by solution exchange using filtration methods, 3) by direct modification of the existing solution conditions, or 4) by other means of solvent exchange. Cells suspended in an appropriate solution are then contacted with certain amphipathic molecules that cause disruption of the cell membrane thus allowing the cell contents to diffuse through the cell wall and into the extracellular medium. Cellular debris is then separated from the soluble extract by sedimentation, flocculation, filtration, chromatographic, or other separation methods.

In a preferred embodiment, yeast cells, for example *Pichia pastoris*, taken directly from a fermentation process are concentrated and then exchanged from growth medium into a specific buffered solution by tangential flow filtration using microporous membranes. The concentrated and solution adjusted cells are then contacted with dimethylamine and/or dimethylamine oxide compounds with alkyl chains of varying length, depending on cell type and solution conditions. In addition, the solution may contain detergents, such as Triton X-100 or polyols, such as glycerol, that enhance the extraction process. The extract of intracellular molecules is then separated from the remaining insoluble slurry by depth filtration, for example, using diatomaceous earth in a plate and frame filter press.

Solution permissivity is dependent on pH, temperature, ionic strength, time, cell concentration and the addition of certain components that enhance the effectiveness or kinetics of cell disruption or molecular stability. Solution pH can be from pH 3 to 11, more preferably 5 to 8, or approximately 6.5 to 8.0. Temperature can range from about 20° C. to 50° C., or more preferably 2° C. to 30° C. Ionic strength can vary from hypotonic to hypertonic conditions, most preferably 0.001 to 3000 mM sodium chloride, or other salt, depending on the properties of the desired target molecule. In preferred embodiments, the ionic strength is below 350 mM, below 250 mM, below 150 mM, below 100 mM, below 50 mM, and below 10 mM, but not lower than 5 mM, 1 mM, 0.01 mM or 0.001 mM.

The "host cells" are cells containing a protein of interest. A "protein of interest" is any protein present in a host cell that one desires to release from the host cell and, optionally, subsequently isolate or purify. Preferably, the protein of interest is a recombinant protein. When the protein of interest is a recombinant protein, it can be produced by any method known in the art. Typically, a gene that encodes the recombinant protein that is desired is inserted into a recombinant molecule. The polynucleotides constituting the gene may be obtained by standard procedures known in the art, such as from cloned DNA (such as a DNA "library"), chemical synthesis, cDNA cloning, or by the cloning of genomic DNA, or fragment thereof, from a desired cell as described in Sambrook, J., et al., Molecular Cloning: A Laboratory Manual, 2d Edition, Cold Spring Harbor Laboratory Press (1989).

Once the gene encoding the recombinant protein has been isolated, it is inserted into an appropriate cloning vector. A large number of vector-host systems known in the art may be used. Possible vectors include, but are not limited to, plasmids or modified viruses, provided that the vector system is compatible with the host cell used. The vectors that can be used include, for example, an *E. coli* cloning vector, bacteriophages such as lambda derivatives, plasmids such as pBR322 derivatives or pUC plasmid derivatives. The cloning vector can be introduced into host cells via transformation, transfection, infection, electroporation, etc., so that many copies of the gene sequence are generated.

Transformation of host cells with a cloning vector that incorporates the gene enables the generation of multiple copies of the gene. Therefore, the gene may be obtained in large quantities by growing transformants, isolating the cloning vector from the transformants and, when needed, retrieving the inserted gene from the isolated cloning vector. Once sufficient copies of the gene sequence have been generated, the gene encoding the recombinant protein, or a functionally active fragment or other derivative thereof, can be inserted into an appropriate recombinant molecule. The recombinant molecule is a polynucleotide expression vector that contains the necessary elements for the transcription and translation of the inserted protein-coding sequence of the recombinant protein. Preferably, the expression vector also includes an origin of replication. The necessary transcription and translation signals can also be supplied by the native gene and/or its flanking regions.

Once a recombinant molecule has been prepared, it is inserted into an acceptable host cell which will grow and divide to produce clones. A variety of host cell-vector systems may be utilized to express the recombinant protein. Suitable host cell-vector systems include, for example, bacterial expression systems, mammalian cell systems infected with a virus, such as a vaccinia virus or adenovirus, insect cell systems infected with a virus such as a baculovirus, microorganisms such as yeast containing yeast vectors, and bacteria transformed with bacteriophage DNA, plasmid DNA or cosmid DNA.

Recombinant molecules containing the gene of interest can be identified by PCR amplification of the desired plasmid DNA or specific mRNA, nucleic acid hybridization, presence or absence of marker gene functions and expression of the inserted sequences.

The host cells, such as *E. coli* cells, transformed with a polynucleotide that encodes a recombinant protein of interest, can be added directly to a reaction vessel. To purify and recover the recombinant protein, the host cells are concentrated to form a concentrated suspension of whole cells. The host cells can be concentrated by any method known in the art. For example, the host cells may be centrifuged. Centrifugation removes water from the host cells and concentrates the cells, forming a cell paste. Centrifugation also separates the host cells from the culture medium. The host cells may be of any type, preferably mammalian, bacterial, yeast, plant, avian, or reptilian. Most preferably, the host cells are yeast cells.

Once a concentrated suspension of cells has been obtained, the cells are contacted with a protein recovery solution. The protein recovery solution comprises one or more detergents and one or more reducing agents. In a particular embodiment, the one or more detergents are amphipathic, charged amines or amine oxides coupled to hydrocarbon chains of varying lengths. In a preferred embodiment, the one or more detergents used are selected from the group consisting of, tributylphosphate, dimethyldecylamine, dimethyltridecylamine, dimethylundecylamine, dimethyldidecylamine, dimethytetradecylamine, dimethylhexadecylamine, dimethyldecylamineoxide, dimethylundecylamineoxide, dimethyldidecylamineoxide, dimethytetradecylamineoxide and dimethyltridecylamineoxide. Preferably, the detergent is not dimethyltridecylamine. Detergents may be used at concentrations ranging from 0.01% up to their solubility limit. Preferably, the concentration of the detergents ranges from 0.05% to 5%, 0.1% to 2%, or is approximately 0.5% or 1% of the total solution. Preferably, the detergents, just prior to their addition to the host cells, are at least 90%, at least 95% or at least 99% pure. In preferred embodiments, the detergents to be added are at least 3 fold, at least 5 fold, at least 10 fold, at least 50 fold, at least 100 fold, at least 200 fold the final concentration of the detergents after addition and dilution in the cell suspension.

In a particular embodiment, the one or more reducing agents are agents are those reducing agents that reduce disulfide bonds and/or maintain sulfhydryl residues in the reduced form. Any such reducing agent or agents may be used. In a preferred embodiment, the one or more reducing agents used are selected from the group consisting of, Dithiothreitol (DTT); Dithioerythiritol (DTE); Cysteine (Cys) and Tris 2-carboxyethyphosphine (TCEP).

Reducing agents may be used at concentrations ranging from 0.1 mM to 100 mM, 1 mM to 25 mM, 2 mM to 10 mM, or about 5 mM. When added to cells suspended in buffer, the reducing agent is preferably at a higher concentration than the final concentration at which the cells are lysed. Preferably, the detergent is at least at a 2 fold, 5 fold, fold or 100 fold higher concentration. The effectiveness of the reducing agent can be determined by titration of free sulfhydryls using Ellman's reagent. Preferably, the reducing agent is Dithiothreitol. Preferably, the reducing agent concentration is 5 mM. Preferably, the reducing agent is added to the extraction buffer just prior to the addition of the detergent followed by incubation at 4° C. for 12 hours. However, the reducing agent may be added before or after the detergent. Preferably, the reducing agent is added prior to the addition of the detergent. In another embodiment, the detergent and reducing agent are added together. In another embodiment, the detergent is added prior to the reducing agent.

In addition to the one or more detergents and reducing agents, in a preferred embodiment, the cells are also contacted with glycerol. Preferably, the glycerol concentration is at least 0.6%, or ranges from 0.6% to 20%, 0.6% to 12%, 0.6% to 6%, 0.6% to 3%, or 0.6% to 1%. Preferably, the glycerol, just prior to addition to the host cells, is at least 90%, at least 95% or at least 99% pure. In preferred embodiments, the glycerol to be added is at least 3 fold, at least 5 fold, at least 10 fold, at least 50 fold, at least 100 fold, at least 166 fold the final concentration of the glycerol after addition and dilution in the cell suspension.

Preferably, the solution is at a pH ranging from pH 5.0 up to pH 8.0. More preferably, the pH ranges from pH 5.5 to 7.4, from pH 6 to 7.4, from pH 7.0 to 7.4, or is approximately pH 7.3.

The recovery of the protein of interest from the cells with the solution of the invention can be carried out at a temperature of from about 2° C. to about 50° C. Preferably, the temperature is from about 2° C. to about 30° C., 2° C. to about 20° C., 2° C. to about 10° C., about 4° C., about 25° C., or at room temperature.

The amount of the detergent and reducing agent solution of the invention used per gram of cells can vary greatly, for example, anywhere from 0.5 mL of detergent and reducing agent solution per gram of cells to 20 mL per gram may be used. Preferably, 2.5–5.0 mL detergent and reducing agent solution per gram of cell paste is used.

The amount of time allowed for lysis of the cells after contacting said cells with the protein recovery solution may be determined by one of skill in the art. For example, cells may be incubated in the presence of the protein recovery solution for 40 minutes up to 72 hours, preferably 90 minutes, 150 minutes, 8 hours or 16–30 hours. Shorter and longer times are also appropriate. In general, the amount of time can be increased when the concentration of detergent is low and decreased when the amount of detergent is high. For example, a protein recovery solution with a 1% detergent concentration is effective after 40 minutes, while a protein recovery solution with a 0.1% detergent concentration should be incubated for 150 minutes or longer. For optimal recovery of protein, the exact amount of time necessary can be determined by a simple time-course experiment at a given concentration of detergent, where concentration of the protein of interest released to the medium is determined over time. After a certain time point, no further increase in released protein will be observed. This time point is the optimal time necessary for lysis of the cells with the chosen concentration of detergent.

After lysis of the cells, the solution can be centrifuged to collect cellular debris in the pellet, leaving the released protein of interest in the supernatant. The supernatant may be processed according to methods known to those of skill in the art to further isolate and purify the protein of interest. The methods utilized to further isolate and/or purify the protein of interest are highly dependent upon the characteristics and properties of the particular protein of interest, and must be determined for each protein. In a particular embodiment, the protein of interest has reactive sulfhydryls. In a particular embodiment, the protein of interest, in its native conformation, has one or more disulfide bonds. In a particular embodiment, the protein of interest is purified in a reduced form, e.g., with free sulfhydryl groups. In a particular embodiment, the protein isolated in a reduced form is folded after purification into its native, oxidized conformation. For methods of folding proteins, see Chaudhuri JB, Refolding recombinant proteins: process strategies and novel approaches. Ann N Y Acad Sci May 1994 2;721:374–85, incorporated herein in its entirety by reference.

In a preferred embodiment, the method of the invention is applied to a large scale process of recovering a biomolecule. A large scale process is a process involving large amounts of host cell biomass. In preferred embodiments, the amount of biomass processed in a single batch according to the methods of the invention is from 1 kg to 50,000 kg, 1000 kg to 20,000 kg, 5000 kg to 10,000 kg, or about 40 kg, 100 kg, 1000 kg or 10,000 kg. In another embodiment, the amount of biomass is greater then 1 kg, greater than 40 kg, greater than 100 kg, greater than 1000 kg, greater than 5000 kg, greater than 10,000 kg, or greater than 20,000 kg. The host cells are generally in fermentation broth at the beginning of the process. The host cells are concentrated in the fermentation broth, by, for example, centrifugation or tangential flow filtration, then the fermentation broth exchanged with 60 mM sodium phosphate, 50 mM NaCl, 5 mM EDTA, pH 7.3 (buffer). The exchange can be performed by any means known to one of skill in the art, for example, by tangential flow filtration using 0.45 μm membrane. The concentrated biomass can be maintained at a constant volume while buffer is added to the biomass at a rate equal to the rate at which liquid was removed from the biomass by the filtration process. A buffer exchange of greater than 50%, greater than 60%, greater than 70%, greater than 80%, greater than 90%, 95%, greater than 95% or approximately 100% may be used. Preferably, the exchange is 90% or more. For example, for 7.6 liters of fermentation broth containing approximately 3 kg of cells, approximately 27 L of buffer may be processed as above which results in a buffer exchange of >95%. The concentrated and buffer exchanged biomass is then modified by the addition of reducing agent, detergent and other compounds, for example, glycerol and tetradecyldimethylamine to concentrations of 5 mM, 6.0% final weight and 0.5% final weight, respectively. The added compounds may be added separately or mixed and added together. Other concentrations, as recited above, may also be used. The mixture may then be incubated with agitation. This incubation may be for any appropriate time and temperature, for example, for 14.5 h at 19° C. The actual concentrations of reducing agents, detergents, time and temperature for any given extraction may be readily determined by one of skill in the art. After incubation, the soluble fraction of the mixture contains large amounts of protein, nucleic acids, lipids and other molecules previously restricted to the cell membrane and cytoplasm. The mixture may be centrifuged, for example at 4000×g for 30 minutes. The supernatant fraction may then be further processed by, for example, filtration through a 1.2 μm and 0.2 μm filters in series.

The following Examples illustrate the preferred embodiments of the process of the present invention and is not limiting of the specification and claims in any way.

EXAMPLES

Large Scale Release of Recombinant Product

*Pichia pastoris* fermentation broth (12.6 Kg) containing 24.4% biomass by wet weight, having a conductance of 30.2 mS/cm and pH of 4.86, was concentrated to 7.6 L. The concentrated biomass was then exchanged into 60 mM sodium phosphate, 50 mM NaCl, 5 mM EDTA, pH 7.3 (buffer) by tangential flow filtration using 0.45 $m^2$ of 0.45 μm membrane. The concentrated biomass was maintained at 7.6 L while buffer was added to the biomass at a rate equal to the rate at which liquid was removed from the biomass by the filtration process. Approximately 27 L of buffer were processed as above which results in a buffer exchange of >95%. The concentrated and buffer exchanged biomass was then modified by the addition of glycerol and tetradecyldimethylamine, separately, to concentrations of 6.0 and 0.5 final weight percent, respectively. The mixture was then incubated with agitation for 14.5 h at 19 ° C. At this point the soluble fraction of the mixture contained large amounts of protein, nucleic acids, lipids and other molecules previously restricted to the cell membrane and cytoplasm. The mixture was then centrifuged at 4000×g for 30 minutes. The supernatant fraction was then further processed by filtration through a 1.2 μm and 0.2 μm filters in series. The resulting clarified extract contained approximately 15 g/L of total protein and 0.8 g/L of the specific heterologous protein of interest. The clarified extract also contained significant quantities of ribonucleic acid, deoxyribonucleic acid and cell derived lipids.

Extraction of Recombinant Product Over Time and at Differing Temperatures

*Pichia pastoris* cells were exchanged into permissive buffer conditions and contacted with 0.5% tetradecyldimethylamine (DMA-C14) and 1% Triton X-100 and 6% glycerol. Samples of the supernatant were taken at various times after incubation at different temperatures, 4° C. and 22° C. The concentration of a specific heterologous (Bot B, or rBoNTB/Hc protein) protein was then determined by an HPLC method specific for that protein. The results are shown in FIG. 1 (4° C.) and 2 (21° C.). The heterologous is released at higher efficiency over time and at the higher temperature, although at 25 hours, the amount of protein released at the two temperatures were indistinguishable when DMA C14 (tetradecyldimethylamine), triton and glycerol or DMA-C14 and glycerol were used. DMA C14 and Triton and DMA C14 were less effective. Other observations, not represented in FIG. 1 or FIG. 2, show that glycerol, Triton X-100 or buffer alone did not extract protein at a level that was detectable.

Non-Selective Recovery of Intracellular Biomolecules

*Pichia pastoris* cells were exchanged into permissive buffer conditions and contacted with 0.5% tetradecyldimethylamine (DMA-C14) and 6% glycerol. Samples were taken after incubation and after clarification (low speed centrifugation and 0.2 μm filtration). The concentration of RNA, DNA, phospholipids, and total protein were measured using commercially available reagent kits. The concentration of a specific heterologous protein (rBoNTB/Hc) of interest was then determined HPLC. The results are in Table 1.

TABLE 1

| Sample/ assay | RNA (mg/L) | DNA (mg/L) | Phospho- lipids (mg/L) | Total protein (g/L) | heterologous protein (mg/L) |
|---|---|---|---|---|---|
| extract | 479 | 61 | 1000 | 7.5 | ND |
| clarified extract | <8 ug/mL | 4 | <50 ug/mL | 6.7 | 0.36 |

The data show that RNA, DNA, phospholipids, a specific heterologous protein, and non-specific total protein were extracted from the cells. This shows that the method is non-selective and therefore generally applicable for the recovery in intracellular molecules from microbial cells. The data also show that DNA, RNA, and lipids are easily removed from the soluble protein fraction of the DMA-C14 glycerol extract (compare the extract to the clarified extract). This is in contrast to mechanical cell extraction methods that result in the formation of colloidal suspensions high in nucleic acid and lipid content. Such colloidal materials are not easily separated from the soluble protein fraction and may complicate protein purification methods. Or, on the other hand, severely limit the recovery of DNA, RNA, lipids or similar molecules if those molecules were the molecules of interest. Thus, the gentle, low shear and non-selective feature of the permeabilization method may facilitate the recovery of non-protein intracellular products such as nucleic acids, lipids, and other molecules not readily obtained from mechanical lysates.

Recovery of Intracellular Biomolecules in the Presence of a Reducing Agent

*P. pastoris* cells expressing the rBoNTA(Hc) protein were suspended (350 g biomass/L extraction buffer) in a solution containing 0.5% DMA-C14 (w/w) and 6% (w/w) glycerol at pH 7.2. One sample was then incubated at 21° C. and a second sample at 4° C. Dithiothreitol (DTT) was then added to a third sample to 4 mM and the sample was incubated at 21° C. DTT was added to a fourth sample to 1 mM and the sample was incubated at 4° C. Aliquots were removed from each of the four samples at the time-points indicated (see FIG. 1), the samples were clarified and the concentration of rBoNTA(Hc) was determined by HPLC. The rBoNTA(Hc) concentration was then plotted as a function of time for the four different treatments. The data are summarized in FIG. 1.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. A method of releasing a protein of interest from host cells comprising contacting the host cells with a detergent, wherein the detergent comprises an amphipathic charged amine or an amphipathic charged amine oxide.

2. The method of claim 1, wherein the detergent is selected from the group consisting of: dimethyldecylamine, dimethyltridecylamine, dimethylundecylamine, dimethyldidecylamine, dimethyltetradecylamine, dimethylhexadecylamine, dimethyldecylamineoxide, dimethylundecylamineoxide, dimethyldidecylamineoxide, dimethytetradecylamineoxide and dimethyltridecylamineoxide.

3. The method of claim 1, wherein the detergent is not dimethyltridecylamine.

4. The method of claim 1, wherein the host cells are *Pichia pastoris* cells.

5. The method of claim 1, further comprising the step of incubating the host cells at a temperature of between about 2° C. and about 50° C.

6. The method of claim 1 wherein the detergent is added to the host cells at a concentration up to two hundred times the concentration of the cells.

7. The method of claim 1 wherein the pH of the host cells ranges from about pH 5.0 to about pH 8.0.

8. The method of claim 1 wherein the host cells are suspended.

9. The method of claim 1, further comprising the step of incubating the host cells from about 40 minutes to about 72 hours.

10. The method of claim 9, wherein the incubation is from about 90 minutes to about 24 hours.

11. The method of claim 1 further comprising contacting the host cells with a reducing agent.

12. The method of claim 11, wherein the reducing agent is selected from the group consisting of Dithiothreitol (DTT); Dithioerythiritol (DTE); Cysteine (Cys) and Tris 2-carboxyethyphosphine (TCEP).

13. The method of claim 12, wherein the reducing agent is at a concentration of from about 0.1 mM to about 100 mM.

14. The method of claim 1, further comprising adding glycerol to the host cells.

15. The method of claim 14, wherein the glycerol comprises a concentration of between about 0.6 to about 20 percent.

16. The method of claim 14, wherein the detergent comprises a concentration of between about 0.01 percent to the solubility limit of the detergent.

17. The method of claim 16, wherein glycerol comprises a concentration of between about 0.6 to about 6 percent.

* * * * *